(12) United States Patent
Van Hoeck et al.

(10) Patent No.: US 6,755,839 B2
(45) Date of Patent: Jun. 29, 2004

(54) ADJUSTABLE SURGICAL GUIDE AND METHOD OF TREATING VERTEBRAL MEMBERS

(75) Inventors: James E. Van Hoeck, Cordova, TN (US); Kevin Foley, Germantown, TN (US); Regis Haid, Atlanta, GA (US); Stephen Papadopoulos, Paradise Valley, AZ (US); Stephen Heim, Wheaton, IL (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/175,221

(22) Filed: Jun. 19, 2002

(65) Prior Publication Data
US 2003/0236526 A1 Dec. 25, 2003

(51) Int. Cl.[7] .............................................. A61B 17/56
(52) U.S. Cl. .......................................... 606/87; 606/90
(58) Field of Search ............................. 606/87, 90, 84, 606/61, 63, 79, 80, 71, 96, 167, 170; 623/17.15, 17.16

(56) References Cited

U.S. PATENT DOCUMENTS

| | | | | |
|---|---|---|---|---|
| 4,289,123 A | * | 9/1981 | Dunn ........................... | 606/61 |
| 5,067,898 A | * | 11/1991 | Dury ............................ | 433/75 |
| 5,620,443 A | * | 4/1997 | Gertzbein et al. ............. | 606/61 |
| 5,895,387 A | * | 4/1999 | Guerrero et al. .............. | 606/71 |
| 6,083,228 A | | 7/2000 | Michelson | |
| 6,117,135 A | * | 9/2000 | Schlapfer ..................... | 606/61 |
| 6,136,002 A | * | 10/2000 | Shih et al. .................... | 606/61 |
| 6,159,214 A | | 12/2000 | Michelson | |
| 6,224,599 B1 | * | 5/2001 | Baynham et al. ............. | 606/61 |
| 6,261,295 B1 | | 7/2001 | Nicholson et al. | |
| 2003/0105463 A1 | * | 6/2003 | Wolgen ....................... | 606/71 |

FOREIGN PATENT DOCUMENTS

DE          201 11 479 U      4/2001

OTHER PUBLICATIONS

U.S Publ. No. 2002/0049444 A1; Apr. 25, 2002; Spinal Fusion Instrumentation System; Benjamin D. Knox; 17 pgs.

* cited by examiner

Primary Examiner—Eduardo C. Robert
Assistant Examiner—David C. Comstock
(74) Attorney, Agent, or Firm—Coats & Bennett, P.L.L.C.

(57) ABSTRACT

A guide and method of using the guide for positioning within a patient between vertebral members for contouring each of the members. The guide comprises a first section and a second section. A first edge is positioned along an edge of the first section, and a second edge is positioned along an edge of the second section. One or more elongated rods extend through the sections. One or both of the sections are movable along the rods to adjust a spacing between the first edge and the second edge. When positioned within the patient, the first edge is aligned along a first vertebral member and the second edge is aligned along a second vertebral manner. A manner of locking the sections is included for preventing the sections from moving relative to each other once the first and second edges are aligned within the patient.

26 Claims, 5 Drawing Sheets

ADJUSTABLE SURGICAL GUIDE AND METHOD OF TREATING VERTEBRAL MEMBERS

BACKGROUND OF THE INVENTION

Current surgical procedures often require a great deal of skill from the surgeon to properly perform the procedure. The procedures may include making fine manipulations by hand using high-speed equipment. One example includes preparing end plates of adjacent vertebrae to receive a graft or inter-body fusion device. Each of the surfaces are prepared in the adjacent end plates using a high-speed burr or other cutting instrument that is held and manipulated by the surgeon. It is difficult for the surgeon to create consistent surfaces on the end plates using a hand-held instrument. The tactile and visual feedback received from the surgeon may further be more difficult because the surgeon is operating in a very small space.

Current surgical procedures may also be time consuming. It may be difficult for the surgeon to determine the amount of preparation required for each of the opposing surfaces. A trial-and-error routine is performed as the surgeon removes a first amount of material from one or both surfaces and determines whether the spacing is adequate for receiving the interbody device. If the spacing is not adequate, the surgeon removes an additional amount from one or both of the surfaces. This routine continues until the proper amount has been removed and the surfaces are adequately prepared. The surgeon is careful not to remove too much from either surface, and instead tends to remove small increments each time. It would be advantageous if the surgeon had a manner of more accurately determining the amount of material to be removed from one or both surfaces, such that the trial-and-error routine could be reduced, or eliminated.

Many surgical devices in use today are sized for a particular application. These devices have limited utility because there is no manner of adjusting the size to fit the particular application.

SUMMARY OF THE INVENTION

The present invention is directed to an adjustable guide for treating two vertebral members. The guide includes a first section having a first edge and a second section having a second edge. At least one of the sections is movable to adjust the distance between the first edge and the second edge. When properly aligned, the first edge is aligned relative to the first vertebral member and the second edge is aligned relative to the second vertebral member.

In one embodiment, one or more elongated rods extend through the first and second sections. One or both of the sections is movable along the elongated rods to adjust the distance between the first section and the second section.

The guide may further include a locking mechanism for preventing the first section from moving relative to the second section. A number of different locking mechanisms may be used to prevent any change in the distance between the two sections.

The guide may also include spacers that extend outward from the guide for inserting between the vertebral members. The spacers may extend outward from one or both of the sections depending upon the application of the guide. The spacers may also be positioned at a variety of locations along the guide, provided there is no interference with the first and second edges.

DETAILED DESCRIPTION

Figure 1:
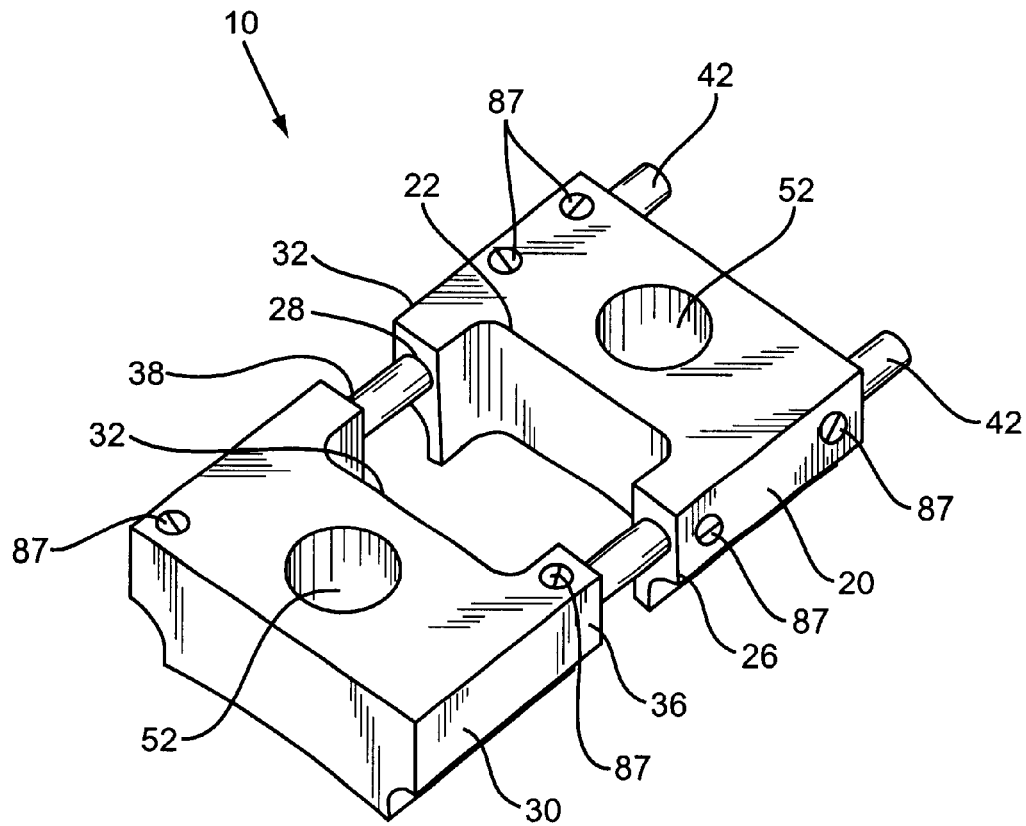
FIG. 1 is a perspective view of one embodiment of the guide of the present invention.

A guide 10 for positioning within a patient between adjacent members for preparing the surface of each of the members. As illustrated in FIG. 1, one embodiment of the guide 10 comprises a first section 20 and a second section 30. A first edge 22 is positioned along an edge of the first section 20, and a second edge 32 is positioned along an edge of the second section 30. One or more elongated rods 42 extend through the sections 20, 30. One or both of the sections 20, 30 are movable along the rods to adjust a spacing between the first edge 22 and the second edge 32. When positioned within the patient, the first edge 22 is aligned relative to a first vertebral body and the second edge 32 is aligned relative to a second vertebral body. A locking means is included for preventing the sections 20, 30 from moving relative to each other once the first and second edges 22, 32 are aligned within the patient.

Figure 4:
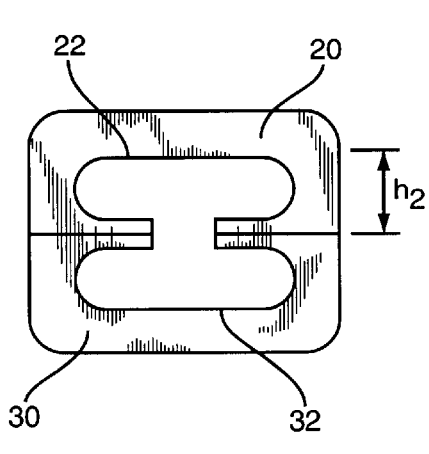
FIG. 4 is a front view of the guide illustrated in FIG. 3.

The first section 20 includes a first edge 22 positioned along a section edge. In the embodiment illustrated in FIG. 1, extensions 26 extend outward along each side of the first edge 22. A second section 30 includes a second edge 32 that extends along a section of the second section 30. In the embodiment illustrated in FIG. 1, extensions 36 are positioned on each side of the second edge 32 and extensions 26 are positioned on each side of the first edge 22. In this embodiment, when the first and second sections 20, 30 are closed, extensions 26 contact extensions 36 and the first edge 22 is spaced away from the second section 30 with an opening being formed therebetween. In another embodiment, the first edge 22 is positioned to directly contact the second edge 32 when the sections 20, 30 are in a closed orientation. The terms "closed", "closed orientation", and the like will be used throughout to mean the first section 20 being in contact with the second section 30. The terms "open", "open orienation", and the like will be used throughout to mean the first section 20 being spaced apart from the second section 30. By way of example, FIG. 1 illustrates the first and second sections 20, 30 in an open orientation and FIG. 4 illustrates a closed orientation.

The first edge 22 and second edge 32 may have a variety of different shapes. In one embodiment, the first edge 22 and second edge 32 are parallel. In one embodiment, the first edge 22 and second edge 32 are maintained in a parallel relationship as the first section 20 and second section 30 are moved between open and closed orientations. The first edge 22 and second edge 32 may have a variety of lengths. In one embodiment, the lengths extend across the entire length of the vertebral members.

In one embodiment, one or more elongated rods 42 connect the first section 20 and the second section 30 and provide a means for moving the first section 20 relative to the second section 30. The elongated rods 42 are positioned along the outer edges of the guide 10 to not interfere with the first and second edges 22, 32. In one embodiment, one of the first and second sections 20, 30 is fixedly attached to the elongated rods 42 and the other sections 20, 30 is movable along the elongated rods 42. By way of example as illustrated in FIG. 1, the second section 30 is fixedly attached to the elongated rods 42 and the first section 20 is movable along the elongated rods 42 such that an opening formed between the first and second edges 22, 32 is adjustable. In another embodiment, both the first and second sections 20, 30 are movable along the elongated rods 42. To allow for adjustment along the elongated rods 42, the sections 20, 30 include openings 28, 38 having a larger size than the elongated rods for moving the sections 20, 30.

A locking means prevents the first section 20 from moving relative to the second section 30. In one embodiment as illustrated in FIG. 1, the first and second sections 20, 30 each include an aperture 52 sized to receive a fastener 62. A first fastener 62 within the aperture 52 of the first section 20 connects the first section 20 to the first vertebral body 210, and a second fastener 62 within the aperture 52 of the second section 30 connects the second section to the second vertebral body 220 as illustrated in FIG. 2.

Figure 2:
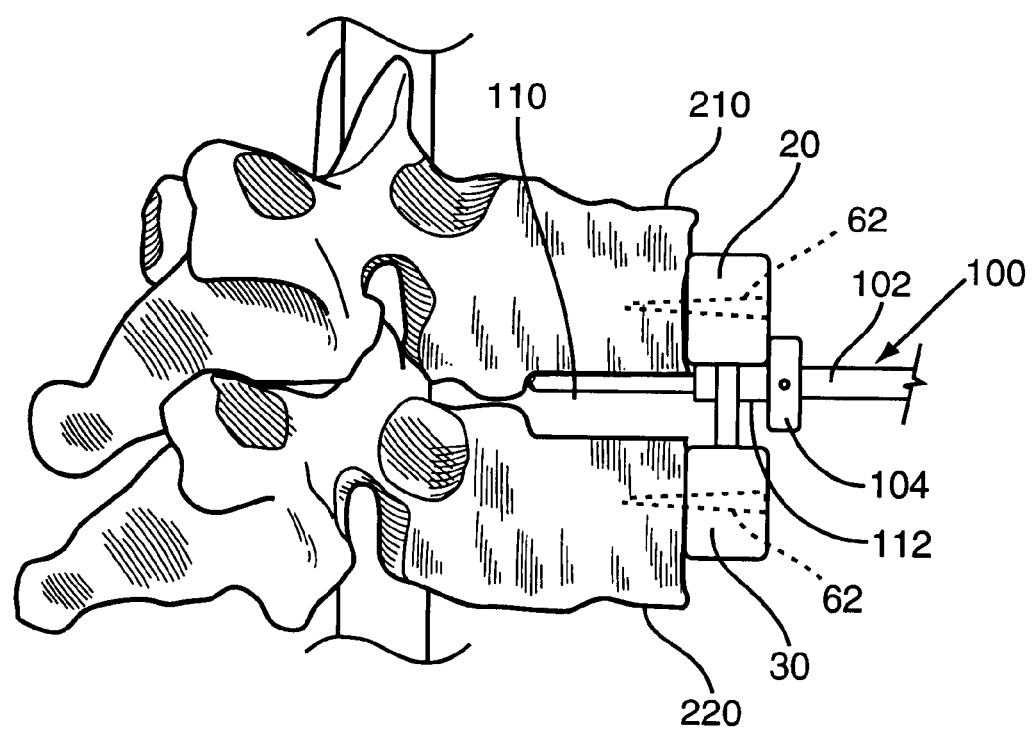
FIG. 2 is a side view of the guide mounted to adjacent vertebral members with a contouring tool in use to shape the vertebral members according to one embodiment of the present invention.

As illustrated in FIG. 2, a bone shaping device 100 is inserted within the guide 10 to shape and contour the vertebral members 210, 220. One embodiment of the device 100 includes a shaping tool 110, and a sleeve 102. The shaping tool 110 extends outward to contact the vertebral members 210, 220. The shaping tool 110 includes a sharpened tip at a distal end, and cutting surfaces that extend along the sides. The sleeve 102 includes an alignment surface 112 that contacts the first and second edges 22, 32 for positioning the shaping tool 110 relative to the vertebral members 210, 220. In one embodiment as illustrated in FIG. 2, the sleeve 102 further includes a flange 104. The flange 104 extends outward from the sleeve 102 and contacts the surface of the guide 10 to control the depth of the shaping tool 110. The position of the flange 104 can be adjusted to control the depth of the shaping tool 110.

The use of the guide 10 can be described with reference to FIG. 2. The guide 10 is aligned within a patient between the two vertebral members 210, 220. The first section 20 and second section 30 are separated the necessary distance such that the first edge 22 is aligned on one vertebral body 210 and the second edge 32 is aligned on the second vertebral body 220. The alignment process may include initially positioning one of the edges 22, 32 relative to a first vertebral member, and then positioning the second edge relative to a second vertebral member. Alternatively, both edges 22, 32 may be moved concurrently and aligned. The fasteners 62 are placed within the apertures 52 of the first and second sections 20, 30 to maintain the position of the edges 22, 32. The bone shaping device 100 is then positioned within the guide 10. The alignment surface 112 is moved along one of the edges 22, 32 with the shaping tool 110 contacting one of the vertebral members 210, 220. The shaping process may include contouring the vertebral members 210, 220 in a number of different movements with the shaping tool 110 extending outward from the sleeve 102 an additional amount during each pass to shape an additional amount. In one embodiment, the first edge 22 and the second edge 32 are parallel and the shaping tool 110 contours parallel surfaces on the vertebral members 210, 220. When the contouring is complete, the fasteners 62 are removed and the guide 10 is removed from the patient.

Figure 3:
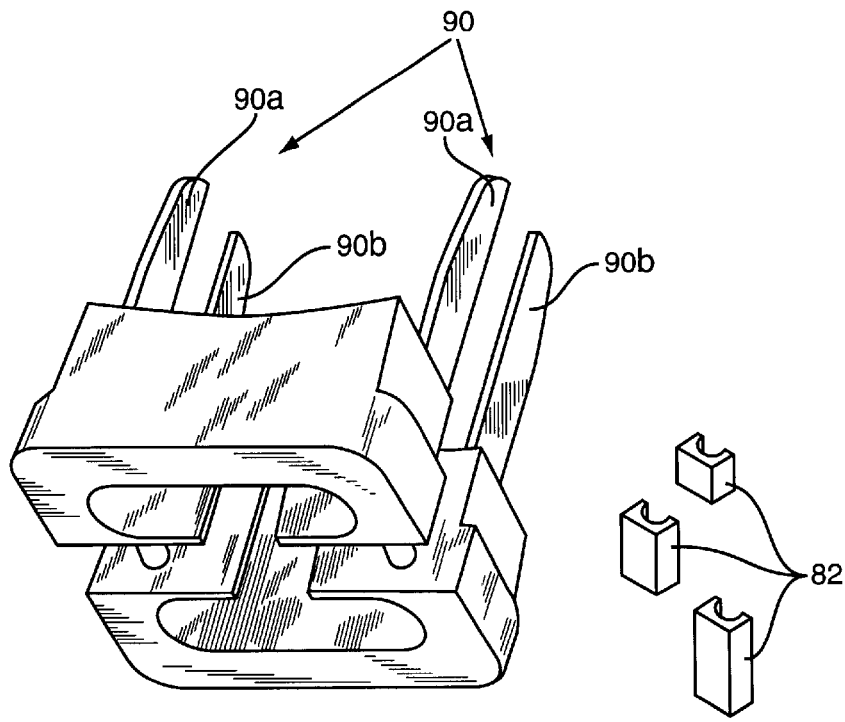
FIG. 3 is a perspective view of a guide constructed according to another embodiment of the present invention.

Other types of locking means may be used for preventing the guide 10 from closing. As illustrated in FIG. 3, spacers 82 are positioned on the elongated rods 42 between the first and second sections 20, 30 to prevent closing. The spacers 82 include indentations that conform to the dimensions of the elongated rod 42. The spacers 82 may be of different lengths to control the spacing between the first and second edges 22, 32. In another embodiment, the spacers 82 are positioned between the first and second sections 20, 30 but are not connected to any members.

Figure 7:
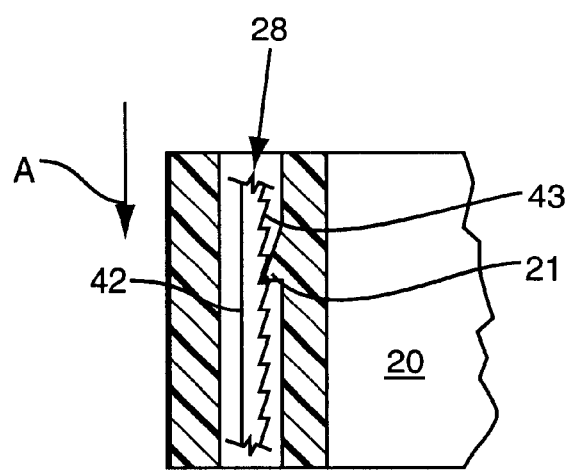
FIG. 7 is a partial side view of a section of the guide and a section of the elongated rod having angled edges according to one embodiment of the present invention.

FIG. 7 illustrates another embodiment of a locking means. The elongated rod 42 includes angled teeth 43. The interior of the opening 28 includes one or more ridges 21 that extend outward to mate with the teeth 43. The angle of the teeth 43 and ridges 21 provide for the two members to slide over each other when the guide 10 is opened by movement illustrated in the direction of arrow A. Closing movement in the direction opposite of arrow A is prevented as the ridge 21 contacts the teeth 43. In this embodiment, the guide 10 can be opened but cannot be closed. This embodiment illustrates the angled teeth 43 and ridge 21 positioned relative to the first section 20 but one skilled in the art will understand that this configuration may be positioned relative to the second section 30, or to both the first and second sections 20, 30. In another embodiment, a ratcheting mechanism is used for locking the sections 20, 30.

In another embodiment of locking the edges 22, 32 relative to one another at a fixed distance as illustrated in FIG. 1, couplers 87 extend between the sections 20, 30 and the elongated rods 42. The couplers 87 are mounted on the sections 20, 30 and tighten against the elongated rods 42 to prevent movement. The couplers 87 are adjustable between a first orientation to allow the section to move relative to the elongated rods 42, and a second orientation that prevents relative movement. Couplers 87 may be mounted in one or both sections 20, 30 of the device 10. The couplers 87 may be mounted on a front face of the sections 20, 30, a side edge, or the back face. In one embodiment, couplers 87 have a mount for mating with a tool to tighten and loosen the fasteners. In one embodiment, the couplers 87 are flush with the surface of the sections 20, 30 when positioned in the tightened, second orientation. In one embodiment, the couplers 87 are set screws.

The first edge 22 and the second edge 32 may have a variety of different configurations. One embodiment is illustrated in FIG. 1 illustrates the edges 22, 32 being parallel and in the closed position the interior edges of the first and second sections 20, 30 forming a substantially rectangular opening. FIGS. 3 and 4 illustrate first and second edges 22, 32 being substantially parallel with the interior edges forming a substantially "H-shaped" configuration. In another embodiment not illustrated, edges 22, 32 directly contact when the guide 10 is in the closed configuration. In another embodiment illustrated in FIG. 6, the first and second edges 22, 32 are curved and form a substantially "curved-H" configuration.

Figure 5:
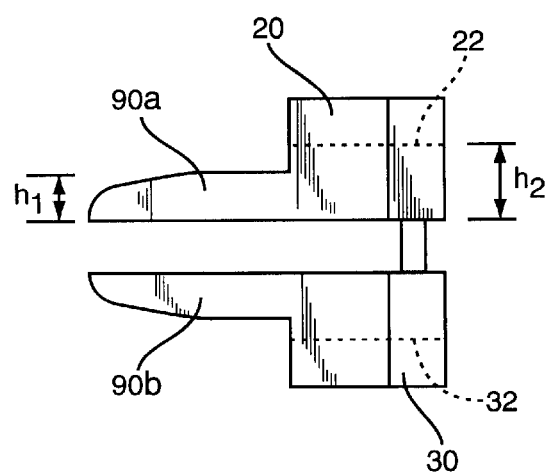
FIG. 5 is a side view of the guide illustrated in FIG. 3.
Figure 6:
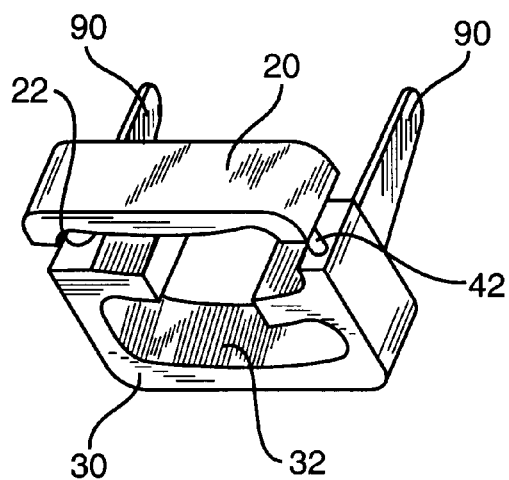
FIG. 6 is a perspective view of a guide constructed according to another embodiment of the present invention.

One or more spacers 90 may extend outward from a rear face of the guide 10 and fit between the vertebral members 210, 220. In one embodiment, the spacers 90 extend outward at an angle of about 90 degrees. Other embodiments include the spacers 90 extending outward at a variety of different angles. The spacers 90 may be positioned at a variety of positions across the width of the guide 10. In one embodiment, spacers 90 are at a position flush with an outer edge of the guide. In another embodiment, spacers 90 are positioned inward of the outer edge of the guide 10. In one embodiment, spacers 90 have a tapered portion adjacent to the end that assists in inserting the guide 10 between the vertebral members 210, 220 as illustrated in FIGS. 3, 5, and 6. The tapered portion may extend along all or a portion of the total spacer length. In another embodiment, the ends are rounded to again ease insertion between the vertebral members 210, 220.

Spacers 90 may extend outward from one or both of the sections 20, 30. By way of example, the spacers 90 in FIGS. 3, 4 and 5 extend outward from both the first and second sections 20, 30. The spacers 90 on each of the sections 20, 30 have a height so as not to interfere with the edges 20, 30. As illustrated in FIG. 5, spacers 90a on the first section 20 have a height h1 that is less than the distance between the edge and the first edge 22, illustrated as height h2. Likewise, the spacers 90b of the second section 30 are sized to have a height less than the distance between the surface and the second edge 32. This size provides that the spacers 90a, 90b do not interfere with the first and second edges 22, 32 aligned with the vertebral members 210, 220. If the spacers had a greater height, the vertebral members 210, 220 would be spaced apart a distance such that the first and second edges 22, 32 would be positioned, within the disc space between the vertebral members 210, 220. In one embodiment, one spacer extends outward from the first section 20 and one spacer extends outward from the second section 30.

First and second sections 20, 30 can have a number of different shapes and configurations. The sections 20, 30 may be substantially similar as illustrated in embodiments of FIGS. 1 and 3. In other embodiments, the two sections 20, 30 are different. As illustrated in FIG. 6, the first section 20 is smaller than second section 30. The first section 20 includes the first edge 22. The second section 30 includes the second edge 32 and a large portion of the remainder of the overall guide body.

The guide 10 can be positioned at a variety of orientations to contour different amounts of the vertebral members. In the embodiment illustrated in FIG. 2, the guide 10 is positioned to contour substantially the same amount of material from each of the vertebral members 210, 220. In another embodiment, the guide 10 is positioned to contour a larger amount of one of the vertebral members 210, 220. The embodiment illustrated in FIG. 2 is applied to the anterior side of the vertebral members 210, 220. However, the guide 10 can be applied to other sections of the vertebral members 210, 220. The guide 10 can be adjusted to fit within different sections of the spine. In one embodiment, the guide 10 is applied to the cervical spine. In other embodiments, the guide 10 is applied to the thoracic and lumbar areas of the spine.

In the embodiment illustrated in FIG. 1, two elongated rods 42 connect the first section 20 and the second section 30. In another embodiment as illustrated in FIG. 6, a single elongated rod 42 connects the sections 20, 30. In another embodiment, more than two elongated rods 42 connect the two sections 20, 30. The elongated rod 42 may have a variety of different cross-sectional shapes and sizes.

Figure 8:
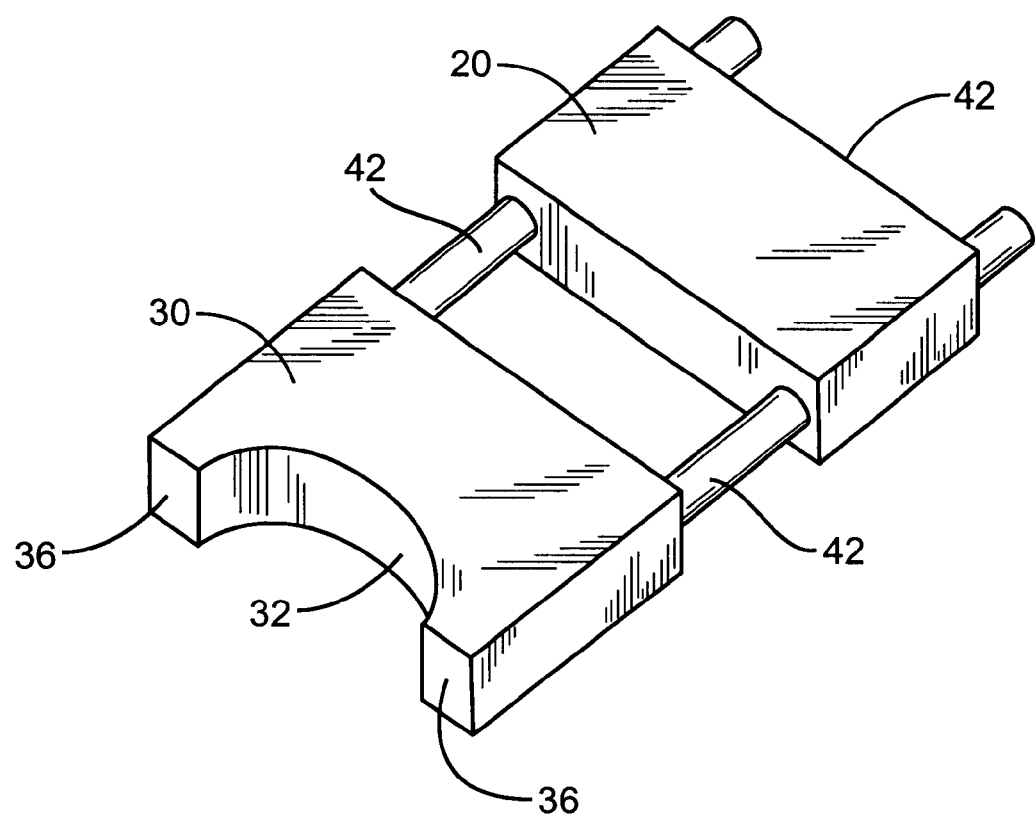
FIG. 8 is a perspective view of another embodiment of the guide constructed according to the present invention.

FIG. 8 illustrates another embodiment of the guide 10 with the first and second edges 22, 32 positioned on outer edges. The sections 20, 30 may be moved apart a given distance along rods 42 such that the edges 22, 32 are aligned relative to the vertebral members. Edge 22 has a substantially straight orientation, while edge 32 includes extensions 36. Various orientations and embodiments or the edges 22, 32 are contemplated within the present invention.

The device 100 may be powered by a number of different sources to provide a rotational or oscillating motion to the shaping tool 110. A variety of different power sources may drive the device 100. Embodiments include a rechargeable battery, gas turbine mechanism, and any standard electrical source, such as 110 volt, 60 cycle power sources, with or without a transformer to reduce the voltage as necessary.

The present invention may be carried out in other specific ways than those herein set forth without departing from the scope and essential characteristics of the invention. The present invention may be used for other applications such as knee surgery, elbow surgery, and others. In one embodiment, the first section 20 and second section 30 are both substantially flat. In another embodiment, sections 20, 30 are curved. The guide 10 may be constructed of a variety of different materials. In one embodiment, the guide 10 is constructed of stainless steel. In one embodiment, couplers 87 mount directly into the elongated rods 42 and do not enter into the sections 20, 30. The present embodiments are, therefore, to be considered in all respects as illustrative and not restrictive, and all changes coming within the meaning and equivalency range of the appended claims are intended to be embraced therein.

What is claimed is:

1. A guide for preparing a vertebral member comprising a body having a first section with a first guide edge extending through the body and a second section with a second guide edge extending through the body, the first section being movable relative to the second section to adjust a distance between the first and second guide edges, and a bone shaping device having a shaping tool sized to move along the first guide edge to contour the vertebral member.

2. The guide of claim 1, wherein the first section has the same shape as the second section.

3. The guide of claim 1, wherein the first guide edge is parallel to the second guide edge.

4. The guide of claim 1, further comprising spacers extending outward from the body between the first guide edge and the second guide edge.

5. The guide of claim 4, wherein a first spacer extends outward from the first section and a second spacer extends outward from the second section.

6. The guide of claim 1, wherein the first and second sections each include an aperture for receiving a fastener for attaching the guide to the vertebral member and an adjacent vertebral member.

7. The guide of claim 1, further comprising locking means to prevent the sections from relative movement and fix the distance between the first and second guide edges.

8. The guide of claim 1, further comprising a flange extending outward from the bone shaping device to be positioned against an outer surface of the first section, the flange being positioned a predetermined distance from a distal end of the shaping tool.

9. The guide of claim 1, further comprising a sleeve positioned around the shaping tool to space the shaping tool from the first guide edge.

10. A guide for contouring a vertebral member comprising:
   a pair of elongated rods spaced a distance apart;
   a first section having a width to extend between the pair of elongated rods and having a first guide edge;
   a second section extending between the pair of elongated rods and having a second guide edge facing the first guide edge of the first section, the second section being movable along the pair of elongated rod to adjust a distance between the first guide edge and the second guide edge; and a shaping tool having a cutting surface that contacts the first guide edge to contour the vertebral member.

11. The guide of claim 10, further comprising a first aperture extending through the first section sized to receive a first fastener to attach to the vertebral member and a second aperture extending through the second section sized to receive a second fastener to attach to a second vertebral member.

12. The guide of claim 10, further comprising a locking means for preventing the changing of the distance between the first guide edge and the second guide edge.

13. The guide of claim 10, further comprising a first spacer and a second spacer extending outward from the first section and a third spacer and a fourth spacer extending outward from the second section.

14. The guide of claim 13, wherein the first and second spacers are positioned an equal distance from an interior edge of the first section between the interior edge and the first guide edge.

15. A method of positioning a guide relative to a first vertebral member and a second vertebral member, the method comprising the steps of:

a. positioning a guide between the first vertebral member and the second vertebral member, the guide comprising a first section with a first edge and a second section with a second edge;

b. moving the first section relative to the second section to adjust the distance between the first edge and the second edge;

c. adjusting the guide with the first edge aligned relative to the first vertebral member and the second edge aligned relative to the second vertebral member; and d. moving a bone shaping device along the first edge to contour the first vertebral member and moving the bone shaping device along the second edge to contour the second vertebral member.

16. The method of claim 15, wherein the first edge and the second edge are parallel during the step of moving the first section relative to the second section to adjust the distance between the first edge and the second edge.

17. The method of claim 15, further comprising locking the guide to prevent the first section from moving relative to the second section.

18. The method of claim 15, further comprising contouring the first vertebral member and the second vertebral member with a first vertebral member edge being substantially parallel with a second vertebral member edge.

19. A method of contouring a first vertebral member and a second vertebral member comprising the steps of:

a. positioning a guide relative to the first vertebral member and the second vertebral member, the guide having a first section with a first guide edge and a second section with a second guide edge;

b. adjusting the first guide edge relative to a second guide edge by moving the guide between a closed orientation and an open orientation with the first guide edge being parallel to the second guide edge while moving between the closed orientation and the open orientation;

c. aligning the first guide edge with the first vertebral member and aligning the second guide edge with the second vertebral member; and d. moving a bone shaping device along the first guide edge to contour the first vertebral member and moving the bone shaping device along the second guide edge to contour the second vertebral member.

20. The method of claim 19, further comprising attaching the guide by inserting a first fastener through a first aperture within the first section and into the first vertebral member and inserting a second fastener through a second aperture within the second section and into the second vertebral member.

21. The method of claim 19, further comprising locking the guide to prevent the first section from moving relative to the second section.

22. A method of preparing opposing surfaces of a first vertebral member and a second vertebral member, the method comprising the steps of:

positioning a guide between the first vertebral member and the second vertebral member, the guide comprising a first section and a second section;

moving the first section relative to the second section and aligning a first edge of the first section with the first vertebral member and aligning a second edge of the second section with the second vertebral member;

moving a bone shaping device along the first edge and contouring the first vertebral member; and moving the bone shaping device along the second edge and contouring the second vertebral member.

23. A guide for contouring a vertebral member comprising:

a first section with a first edge having an extension and a contouring edge recessed from the extension;

a second section having a second edge;

an elongated rod attached to the first section and the second section;

the first section and second section being positionable along the elongated rod between a first orientation with the first edge spaced apart from the second edge, and a second orientation with the extension contacting the second edge and the contouring edge being spaced from the second edge.

24. The guide of claim 23, further comprising the second edge having a second extension and a second contouring edge recessed from the second extension, the second extension contacting the extension in the second orientation with the second contouring edge spaced from the contouring edge of the first section.

25. The guide of claim 23, further comprising a second extension extending from the first edge, the contouring edge being between the extension and the second extension.

26. The guide of claim 23, wherein the elongated rod extends through the extension of the first edge.

* * * * *